United States Patent [19]

Stephen et al.

[11] 4,235,230

[45] Nov. 25, 1980

[54] IODINE COMPOSITION AND METHOD FOR PREVENTION AND TREATMENT OF DIALYSIS INDUCED PERITONITIS

[75] Inventors: Robert L. Stephen; Carl Kablitz; Dietz van Dura; Curtis L. Atkin; Stephen C. Jacobsen, all of Salt Lake City, Utah

[73] Assignee: University of Utah, Salt Lake City, Utah

[21] Appl. No.: 11,356

[22] Filed: Feb. 12, 1979

[51] Int. Cl.³ .................... A61J 7/00; A01N 59/12
[52] U.S. Cl. ..................... 128/213 A; 128/213 R; 424/150
[58] Field of Search ................ 128/213 A, 213 R; 424/150

[56] References Cited

U.S. PATENT DOCUMENTS

| 3,817,860 | 6/1974 | Lambert et al. | 424/150 |
| 4,133,891 | 1/1979 | Nolph | 128/213 A |

FOREIGN PATENT DOCUMENTS

| 1615260 | 2/1961 | Canada | 424/150 |

OTHER PUBLICATIONS

"A Home Peritoneal Dialysate Delivery System", *Trans. Amer. Soc. Artif. Int. Organs,* Tenckhoff et al., vol. XV, 1969, pp. 103–107.

*Primary Examiner*—Robert W. Michell
*Assistant Examiner*—Thomas J. Wallen
*Attorney, Agent, or Firm*—Thorpe, North & Gold

[57] ABSTRACT

A composition and method for use with peritoneal dialysis patients for preventing or treating dialysis induced peritonitis. The method utilizes a flush solution of normal saline to prepare the peritoneal cavity for infusion of a dilute iodine solution which operates to kill pathogenic organisms contained therein. The dilute iodine solution has a combination $I_2$ and HIO concentration in the approximate range of 0.1 ppm to 15 ppm and requires residence time of less than five minutes to provide an effective kill. The serial application of flush and dilute iodine solutions may be applied as part of a regular peritoneal dialysis program to prevent peritonitis or may be used with greater frequency as treatment for existing dialysis induced peritonitis.

17 Claims, No Drawings

IODINE COMPOSITION AND METHOD FOR PREVENTION AND TREATMENT OF DIALYSIS INDUCED PERITONITIS

BACKGROUND OF THE INVENTION

1. Field of Invention

This invention relates to products and methods useful in the prevention and/or treatment of peritonitis conditions such as that which occurs as a consequence of the administration of peritoneal dialysis treatments.

2. Prior Art

The historical transition of peritoneal dialysis from a first clinical attempt in 1923 to a viable life-support system for current patients suffering from renal failure or similar life threatening disorders has been marked with numerous problems which have challenged its acceptance by the medical profession. Chief among these obstacles has been an unacceptably high incidence of peritonitis induced by entry of pathogenic bacteria through access sites used for infusion of dialysate fluids. This "dialysis induced" peritonitis is to be distinguished from "surgical" peritonitis which often accompanies rupture of viscera such as appendix, gall bladder, bowel, etc. Surgical peritonitis presents a uniquely distinguishable environment because of the considerable amount of debris (pus, fibrin and pieces of necrotic tissue) which is contained within the peritoneal cavity.

Dialysis induced peritonitis, however, refers to inflammation of the peritoneum and viscera contained therein by bacteria or fungi, in the absence of concurrent tissue damage, such as from rupture or perforation. Vaamonde et al, for example, have demonstrated that as many as 25% positive cultures of organisms have been present in sample fluids of 142 dialyses. Of these patients with positive cultures, 6.3% contracted clinical peritonitis, an overall incidence rate of 1.6%. Vaamonde, Michael, Metzger, Carroll, "Complications of Acute Peritoneal Dialysis," J Chron Dis 28: 637, 1975. The actual probability of occurrence of dialysis induced peritonitis (hereinafter referred to as "DIP") varies with different methods of peritoneal dialysis.

Peritoneal dialysis was originally accomplished by the manual exchange technique with the use of hanging bottles (1 liter volume) whose contents drained into the peritoneal cavity by means of a catheter. Since a considerable volume of dialysate was normally required, several changes of bottles occurred during each treatment. Because of the high incidence of peritonitis (3%–10% of all dialyses performed) new methods were developed to avoid the use of 1 liter bottles. Fluid delivery systems were automated and coupled to a large reservoir (40 liters) or dialysate proportioning systems which reduced the number of connect-disconnect steps, with an accompanying reduction in exposure to hostile bacteria. With increased attention to strict sterile techniques, these procedures reduced infection rates down to about 0.2% of the total number of dialyses performed.

These two procedures remained as the primary peritoneal dialysis techniques for many years. Government financial assistance became available for patients suffering from End Stage Renal Disease (ESRD) in 1973. With this added financial support, many more patients turned to dialysis centers for life support treatment. As many as 40,000 patients in the U.S.A. are currently relying on dialysis as a life support system, and the number continues to grow. Treatment options available to those patients treated by peritoneal dialysis consist of (1) use of expensive automated equipment, either in a dialysis center or at home, or (2) use of 2 liter bottles or plastics bags of sterile dialysate as a manual exchange method. Neither alternative is pleasant, in view of the life-long inconvenience and expense of the former automated method and the high risk of peritonitis associated with the latter manual exchange method.

In 1977, a variation of the manual exchange method was introduced under the description "Continuous Ambulatory Peritoneal Dialysis" (CAPD). This method provides continuous presence of dialysate within the peritoneal cavity, except during periods of drainage and instillation of fresh solution which is to be effected 4–5 times daily. Using this method the patient experiences new freedom and demonstrates better health and improved appetite. This results, in part, from the fact that the patient is able to perform the drainage and refill within the comfort of his own home without the necessity of installing expensive immobilizing, high technology equipment.

Despite the improvement of CAPD in methodology, the risks of peritonitis are still a major obstacle to acceptance of nonautomated dialysis procedures. It therefore appears that CAPD and similar manual exchange methods can only be successful if techniques for prevention and treatment of DIP are realized. This conclusion is verified by the following experience reports:

1. One group of patients treated under CAPD contracted DIP on the average of once every 10 weeks, Popovich, Moncrief, Nolph, Ghods, Twardowski, Pyle, "Continuous Ambulatory Peritoneal Dialysis," Ann Intern Med., 88,4: 449–456, April 1978. This was later improved to a 1 in 14 weeks average.
2. In a second group practising CAPD, of 41 original patients, five withdrew permanently. Seven others discontinued CAPD on a temporary basis due to DIP. Robson, Oreopoulos, "Continuous Ambulatory Peritoneal Dialysis: A Revolution in the Treatment of Chronic Renal Failure," Daily & Transp 7,10: 999–1003, October 1978.
3. The present inventors, after introducing a subcutaneous catheter method, dialyzed 45 patients by manual exchange for a total of 490 patient weeks (approx. 1470 dialyses). Sixteen episodes of DIP occurred, a rate of 1.1% of all dialyses performed.

Although improved techniques have reduced DIP from the original 3–10% rate incurred during manual exchange peritoneal dialysis, the 0.2 to 0.3% rate of automated dialysis still remains the safest of peritoneal dialysis methods. Therefore, assuming that time on such machines is available, patients must determine whether they can accept the inconvenience and immobilization attendant upon the use of a large and noisy dialysis machine, or assume both the freedom and the risk of DIP accompanying manual exchange techniques.

Once contracted, DIP generally requires extended treatment with antibiotics specifically selected for the infecting bacteria. Such treatments usually require several weeks and are complicated by the fact that DIP may be caused by numerous organisms, including *staphylococcus aureus*, Klebsiella, *staphylococcus epidermidis*, dipheroids, *E. coli*, *streptococcus fecalis*, pseudomonas, fungi and even mycobacteria (tuberculosis-like organisms). Although treatment by use of antibiotics is effective, prevention with antibiotics remains impractical because of the many types of possible infections organism. With respect to DIP patients, both prevention and treatment are particularly significant because peritonitis threatens the very existence of the patients' critical life-support system.

OBJECTS AND SUMMARY OF THE INVENTION

It is therefore an object of the present invention to reduce occurrence rates of DIP in both manual and automated systems.

It is a further object of this invention to provide a method of prevention of DIP which is compatible with all forms of manual exchange dialysis, including CAPD.

It is an object of the present invention to provide products whose use within the peritoneal cavity is effective in prevention or treatment of DIP.

It is an additional object of the subject invention to provide methods of prevention and/or treatment of DIP which can be practiced both clinically and at a patients' private residence.

It is a further object to provide a method or treatment for DIP which is administered with apparatus normally used to effect peritoneal dialysis.

These and other objects are realized in the subject composition and method for preventing or treating dialysis-induced peritonitis by destruction of pathogenic organisms contained within the peritoneal cavity. The method involves the steps of:

1. Preparing a first physiological solution which is free of protein material and of reducing substances which are capable of converting $I_2$ or $HIO$ to $I^-$;
2. Preparing a second physiological solution having a combined $I_2$, $HIO$ concentration in the range of 0.1 to 15 ppm;
3. Flushing a patients' peritoneal cavity with said first solution to remove materials comprising said reducing substances and protein material contained within said cavity; and
4. Contacting said cavity with said second solution for a period of at least 30 seconds.

The combined effect of clearing the peritoneal cavity of iodine deactivating constituents and then applying a dilute iodine solution to destroy remaining bacteria, provides a profound improvement in prevention of peritonitis for patients who are continually being exposed to pathogenic organisms. Furthermore, this method has demonstrated a remarkable cure efficiency in treating early existing peritonitis conditions caused by peritoneal dialysis treatments.

Other objects and features will be apparent to those skilled in the art from the following detailed description of the preferred embodiments and method of practicing the invention.

DETAILED DESCRIPTION OF THE INVENTION

The present invention comprises a two-stage process for obtaining an effective kill of pathogenic organisms should they be present, within the peritoneal cavity of a patient undergoing peritoneal dialysis. Whereas previous techniques have relied on antibiotics and sterility techniques for prevention of such peritonitis, the subject invention presents a new direction involving the nonselective destruction of virtually all pathogenic bacteria.

This invention comprises the serial use of two solutions which represent the two suggested stages of the subject treatment. The first solution consists of a fluid medium or solvent which is compatible for in vivo use in human patients (herein referred to as a "physiological" solution). Normal saline solution is an excellent fluid medium for this purpose and has the advantage of present commercial availability in sterile plastic bags or bottles. Other useful fluids include Ringers Solution or other lactate or acetate solutions.

The first stage of the present method involves flushing sufficient solution through the peritoneal cavity to remove most of the residual dextrose remaining from the immediately preceeding dialysis treatments or to dilute it to innocuous levels with respect to the active constituents of the second solution. In addition, the first fluid assists in removal of other deactivating debris such as fibrin and other protein material.

The amount of solution will naturally depend on the age and size of the patient, as well as the amount of material to be removed. Infants, for example, may only require 50 ml of first solution where a full-grown adult may need 2–3 liters. A precise amount of solution is not critical, however, since dilution and removal of deactivating debris is not a function of stoichiometry. Any doubt as to sufficiency can be safely resolved in favor of a more generous volume.

After completion of the first stage of treatment, the second solution may be effectively applied. Failure to properly flush the peritoneal cavity in accordance with the previous discussion would tend to negate any value of the second stage of treatment. In fact, the use of the first solution is primarily a preparatory flush to enable the subsequent second stage of treatment.

With deactivating constituents removed, the pathogenic bacteria are destroyed by infusion of a dilute solution of iodine. This treatment has been shown to be effective where intraperitoneal conditions can be modified to provide several minutes of life for the free iodine as illustrated by the previous discussion of stage one of the process. It is this uncountered presence of free iodine from the second solution that gives rise to the desired germicidal action. Following introduction of such preventive iodine treatments in a group of peritoneal dialysis patients, the frequency of DIP was reduced from 1/30.6 pt. weeks to 1/182 pt. weeks. The probability of such a reduction occurring by chance is less than 5%.

The antiseptic effect of iodine has been known for many years; however, its effectiveness in vivo is questionable, particularly in the peritoneal cavity when concurrent tissue damage is evident. The adverse prior art is illustrated in data developed by application of povidine-iodine (Iodine=1000 ppm) in dosage amounts yielding about 20 mg of free iodine per Kg of body weight. The experimental class was composed of 44 dogs and 50 rats which were intentionally infected with surgical peritonitis. The test animals were divided into a control group, a group treated with antibiotics and a third group treated with the stated iodine. In essence, all dogs treated with the povidine-iodine died, contrary to the less severe results of the control and antibiotic groups. Lagard, Bolton, Cohen, "Intraperitoneal Povidine-Iodine in Experimental Peritonitis," Ann Surg 187,6: 613–619, 1978.

The present invention develops a different approach for the use of iodine, involving dilution to very low concentrations. In such dilute solutions, the following equilibrium occurs:

$$I_2 + H_2O \rightleftharpoons HIO + H^+ + I^-$$

It is apparent that this reaction is pH dependent. At low pH (approximately 5) elemental iodine predominates, while at higher pH (about 8) most $I_2$ is converted to hypoiodous acid (HIO). Bacteriologically this is not of major concern because HIO appears to be the more microbicidal of the two, except perhaps with respect to E. Histolytica.

To ensure nontoxic levels, the combined concentration of $I_2$ and HIO is maintained below 15 ppm, and preferably between 1–6 ppm. Although most physiological solutions are suitable solvents for iodine, the solution should not contain reducing substances which convert the iodine to iodide ion, since the latter has minimal germicidal character. Dextrose, for example, operates in this manner and thereby deactivates the iodine as a disinfectant. It is this reducing action which prevents the direct addition of iodine to peritoneal dialysate solution which usually contains dextrose. Hence, the subject invention requires a two-stage process of treatment.

In addition, mere infusion of dilute iodine solutions (defined herein as solutions with less than about 15 ppm) to the peritoneal cavity would be without effect both because of the residual dextrose and other proteinaceous material such as fibrin contained within the peritoneal cavity. At such dilute concentrations, the iodine is reduced to iodide ion or inactivated by protein molecules, thereby deactivating its germicidal capacity.

To resolve the unacceptable deactivating environment of the peritoneal cavity and the need to avoid toxic concentrations of iodine, the subject two-step method flushes the cavity with the described first solution. The treatment environment is now adapted to support several minutes of life for the $I_2$ and HIO molecules. The low concentration of such molecules in the range of 0.1 to 15 ppm is nontoxic, yet sufficiently strong to destroy virtually all pathogenic organisms. This kill is accomplished by contacting the peritoneal cavity with the dilute iodine for at least 30 seconds and preferably 2–3 minutes, and then draining it therefrom.

Application of the subject invention has been made in two distinct fields relating to dialysis induced peritonitis. The first is the field of prevention, which heretofore has been attempted only with sterility techniques and antibiotics. The second field involves direct treatment of existing DIP.

The field of prevention is undoubtedly the more significant in view of the large number of patients currently involved with manual exchange methods of peritoneal dialysis, which retains such a high rate of DIP infection. Case studies of the subject invention are summerized as follows:

Fifteen patients, 12 of these suffering both diabetes and End Stage Kidney disease treated by manual exchange peritoneal dialysis three times weekly, entered the following protocol. At the completion of each dialysis, the peritoneal cavity was flushed with 2 liters of normal saline in order to remove as much dextrose and protein as possible (the "Preparatory Flush"). Immediately following, one liter of normal saline containing 0.1 ml of 2% Iodine Tincture (a very small amount—barely enough to discolor the saline) which is 2 parts per million, was infused into the peritoneal cavity, allowed to dwell for 4 minutes and then drained—formally completing the dialysis.

These 15 patients have completed 182 patient-weeks (total patients multiplied by total weeks of dialysis) of manual exchange peritoneal dialysis—545 dialyses. The infection rate has been closely followed clinically and by numerous cultures of peritoneal fluid. One infection occured in 182 pt. weeks (1/545 dialyses). No adverse side effects of iodine were noted. Our previous infection rate with manual exchange peritoneal dialysis using the same subcutaneous catheter and the saline flush (but not the succeeding iodine flush) was 1/30.6 patient-weeks-one infection per 91 dialyses. Statistically the difference is significant ($P < 0.05$).

Where patients are participating in CAPD, prevention methods can be implemented with approximately one iodine treatment every 24 hours. This would be accomplished between drain and refill procedures and would therefore present little inconvenience beyond normal procedures involved in the standard 4–5 changes of solution each day. Following draining of the dialysate solution at any one of the daily changes, the patient flushes with the first solution of normal saline. This normally requires 1–7 minutes for infusion, zero to five minutes residence time and 1–7 minutes outflow or drain time. Assuming comparable flow times for the infusion of the iodine solution, the period of interrupted CAPD is approximately 15 to 45 minutes. This short interruption has provided a marked improvement in prevention of DIP.

With respect to treatment of DIP, the subject invention has caused dramatic results. Contrary to the long periods of treatment required with antibiotics, the use of dilute iodine solutions produced 3 cures of early existing DIP (existing less than 48 hours) within one day or less. The same techniques of flushing with saline and contacting with iodine are used, with a slight increase in iodine concentration. The following clinical experiences are summarized.

Prior to the routine introduction of the iodine flush, one of our patients contracted a severe peritonitis caused by a pseudomonas organism which, although maintained under reasonable clinical control by carefully selected antibiotics, did not resolve—every culture revealed a significant bacterial count for over 3 weeks. Therefore, on completion of a particular peritoneal dialysis treatment, the abdominal cavity received a preparatory flush (2 liters normal saline), then a further 2 liters of normal saline containing iodine 2 ppm (2 mg/l) was infused, allowed to dwell in the peritoneal cavity for approximately 3–4 minutes and was then drained out. Some 20 minutes to 30 minutes following this, the patient underwent a moderately severe reaction consisting of high fever and shaking chills which lasted approximately 2–3 hours and then spontaneously subsided. Although both historically and by means of skin tests, the patient had shown no sensitivity to iodine or related compounds, it was initially assumed that this must have been some form of hypersensitivity reaction. However when on the following day and successive days thereafter, cultures repeatedly demonstrated no growth for the first time in 3 weeks, it was concluded that, rather than an iodine reaction, the patient underwent a severe Herxheimer-type reaction following a large "kill" of organisms and subsequent massive release of bacterial toxins. The absence of hypersensitivity to iodine was confirmed following further challenge with Iodine 0.5 ppm→1.0 ppm→2.0 ppm.

Another diabetic patient treated by CAPD contracted peritonitis. This patient had rejected two transplanted kidneys and lived some 300 miles from the dialysis center. On one occasion, she dropped the cap from the peritoneal catheter onto the floor. She picked it up and immediately replaced it, a grotesque breach of sterile technique. Twenty-four hours following this episode, the peritoneal fluid was somewhat turbid and, although there was no fever, mild abdominal tenderness was present. This was good presumptive evidence of peritonitis. The patient was advised to take a sample of fluid immediately to the local microbiology laboratory and to commence doing an $I_2$ flush following every exchange (4½ hour intervals) as a temporary measure. Tests revealed that the fluid taken on the previous day grew a "light growth of gram positive cocci" on the plate. The fluid obtained after iodine treatment showed a few white cells and no organisms under direct gram stain and was plated for culture. The patient was advised to continue $I_2$ wash-outs at the end of each exchange for a further 24 hours and then fall back upon once daily $I_2$ flushes depending on the results of peritoneal fluid culture. Reports of the culture up to 5 days were consistently negative and further culture taken 3 days later was also negative. In the meantime, the peritoneal dialysate was running completely clear and she had no systemic symptomatology whatsoever. Two subsequent cultures of peritoneal fluid have also been negative. Therefore, it was assumed that if an infection were present, it was ablated within 24 hours.

Other patients have been treated for DIP with comparable success. Furthermore, dialysis patients can monitor fluid turbidity upon draining under CAPD and immediately apply dilute iodine treatment. Two such occurrences resulted in apparent cure with only one application, a treatment period of approximately 45 minutes as compared to the more normal 10 days to 4 weeks under antibiotic therapy.

In addition to the surprising and unexpected efficiency of both the prevention and treatment of DIP by dilute iodine solution, other benefits are noteworthy. The procedure is simple and versatile—capable of performance by the patient individually. At such dilute concentrations, there appear to be no adverse side effects. Patients can self-diagnose possible DIP and immediately apply treatment.

These materials can also be packaged in ready-to-use kit form to facilitate home use by the patient. Such packaging might include several plastic bags of normal saline (first solution) and several bags of physiologic solution coupled to an easy-to-mix container of the requisite quantity of iodine, with means for coupling into the peritoneal dialysate delivery system. The convenience of such a DIP prevention/treatment kit for home use could greatly increase the safety of manual exchange dialysis methods, which appears to offer the preferred means of treatment for such patients.

Although preferred forms of the invention have been described herein, it is to be understood that the present disclosure is by way of example and that variations are possible without departing from the scope of the hereinafter claimed subject matter.

We claim:

1. A method for prevention or treatment of dialysis induced peritonitis comprising the steps of:
   (a) preparing a first physiological solution which is free of protein material and of reducing substances capable of converting $I_2$ or HIO to $I^-$;
   (b) preparing a second physiological solution having a combined $I_2$, HIO concentration in the range of 0.1 to 15 ppm;
   (c) flushing a patients' peritoneal cavity with said first solution to remove materials comprising said reducing substances and protein material contained within said cavity; and
   (d) contacting said cavity with said second solution for a period of at least 30 seconds.

2. A method as defined in claim 1, wherein said first solution is selected from the group consisting of normal saline, lactate, and acetate solutions.

3. A method as defined in claim 1, wherein said combined $I_2$ and HIO concentration is in the range of 1–6 ppm.

4. A method as defined in claim 1, wherein said combined $I_2$ and HIO concentration is approximately 2 ppm.

5. A method as defined in claim 1, wherein said flushing step comprises the component steps of infusing the peritoneal cavity with said first solution and immediately draining the solution therefrom.

6. A method as defined in claim 1, wherein at least 50 ml or one liter of said first solution is flushed through the peritoneal cavity of an infant or adult respectively.

7. A method as defined in claim 1, wherein said contacting step comprises the component steps of infusing said second solution into said cavity, allowing the solution to dwell for 0.5 minutes and then draining it therefrom.

8. A method as defined in claim 1, wherein at least 50 ml or one liter of said second solution for an infant or adult respectively is contacted within the peritoneal cavity for a period of 1–5 minutes.

9. A method as defined in claim 1, further comprising a plurality of flushing steps prior to application of said contacting step.

10. A method as defined in claim 1, wherein said flushing and contacting steps are applied as a last phase of peritoneal dialysis treatment.

11. A method as defined in claim 10, wherein said peritoneal dialysis treatment comprises a manual exchange method followed by said flushing and contacting steps as a final step of the dialysis treatment.

12. A method as defined in claim 10, wherein said peritoneal dialysis treatment comprises a continuous, ambulatory method (CAPD) during which the flushing and contacting steps are accomplished between dialysate drain and refill.

13. A method as defined in claim 12, wherein said flushing and contacting steps are performed at least once each 24-hour period.

14. A method as defined in claim 1, wherein said flushing and contacting steps are applied as part of a treatment for existing dialysis induced peritonitis.

15. A method as defined in claim 14, wherein said flushing and contacting steps are applied with each dialysis treatment utilizing manual exchange methods.

16. A method as defined in claim 14, wherein said contacting step is repeated one to six times on at least a first application of dilute iodine as part of the peritonitis treatment.

17. A method as defined in claim 14, wherein the combined concentration of $I_2$ and HIO is approximately 2 to 6 ppm.

* * * * *